(12) United States Patent
Koteva et al.

(10) Patent No.: US 7,169,756 B2
(45) Date of Patent: Jan. 30, 2007

(54) STREPTOGRAMIN ANTIBIOTICS

(75) Inventors: Kalinka Koteva, Hamilton (CA); Tariq Mukhtar, Richmond Hill (CA); Gerard Wright, Cambridge (CA)

(73) Assignee: McMaster University, Ontario (CA)

( * ) Notice: Subject to any disclaimer, the term of this patent is extended or adjusted under 35 U.S.C. 154(b) by 0 days.

(21) Appl. No.: 11/108,558

(22) Filed: Apr. 18, 2005

(65) Prior Publication Data

US 2005/0272646 A1 Dec. 8, 2005

(51) Int. Cl.
*A61K 38/12* (2006.01)

(52) U.S. Cl. .................... 514/9; 435/71.3; 530/317; 530/322

(58) Field of Classification Search ................ None
See application file for complete search history.

(56) References Cited

OTHER PUBLICATIONS

Bolla, et al., Abstract of Papers, 224th ACS National Meeting, Aug. 18-22, 2002.*
Barriere, et al., Curr Pharm Des., 1998, 4(2), 155-180.*
Robinson, et al., Abstracts of papers, 225th ACS National meeting, New Orleans, LA, Mar. 23-27, 2003, ORGN-148, American Chemical Society: Washington, D. C. (2 pages).*

* cited by examiner

*Primary Examiner*—Anish Gupta
*Assistant Examiner*—Satyanarayana Gudibande
(74) *Attorney, Agent, or Firm*—Fish & Richardson P.C.

(57) ABSTRACT

Disclosed is a cyclic peptide antibiotic in which an enzyme-sensitive bond is replaced by an enzyme-resistant bond.

11 Claims, 6 Drawing Sheets

Quinupristin

5

6

7

Tyrocidine

8

STREPTOGRAMIN ANTIBIOTICS

FIELD OF INVENTION

The invention relates to a novel class of antibiotics, the therapeutic use of the antibiotics and methods for their synthesis.

BACKGROUND OF THE INVENTION

Antibiotic resistance is on the rise globally. This is due in part to transferable resistance genes and also to the selective pressure associated with the increased use of antibiotics. In addition to the widespread use in hospitals, there is often broad scale antibiotic prophylactic use in animal husbandry especially where large numbers of animals are kept in close quarters where infections can easily spread. In addition, antibiotics are often used as growth promoters, especially in poultry and pig farming. There is speculation that the wide use of antibiotics in agriculture has contributed to the transfer of antibiotic resistant microorganisms to humans and the increased identification of transferable resistance genes. Thus there is a real need for the development of novel antibiotics that can be used to treat resistant bacterial infections.

Despite being discovered over 50 years ago, the streptogramin antibiotics have only recently seen significant clinical use [1]. The semisynthetic streptogramin formulation Synercid was approved by the FDA in 1999 for the treatment of serious life-threatening infections caused by antibiotic resistant gram-positive bacterial pathogens such as vancomycin-resistant enterococci [2,3]. Streptogramins are produced by various soil bacteria of the genus *Streptomyces* and consist of two chemically distinct components: type A and type B. The type A streptogramins are cyclic hybrid peptide-polyketide macrolactones [4]. Type B streptogramins are cyclic depsipeptides consisting of 6–7 amino acids. These peptides are cyclized via an ester bond between the C-terminatl carboxyl group and the secondary hydroxyl group of an invariant Thr residue at position 2. The mode of action of both type A and type B streptogramins is through inhibition of translation by binding to bacterial ribosomes [5]. The available evidence indicates that binding of the type A component facilitates binding of the type B streptogramins, a phenomenon that results in synergy of action and bacterial cell death [6]. Recent X-ray structure analysis of the 50S ribosomal subunit in complex with these antibiotics has revealed that type B streptogramins block the peptide exit tunnel while the type A streptogramins bind to the peptidyl transfer center [7].

The only clinically approved streptogramin in North America, Syncercid, is a combination of dalfopristin (type A), and quinupristin (type B). Despite the relatively recent clinical introduction of this antibiotic, resistance to each component is well documented (reviewed in [8]). This may be the result of the fact that streptogramins have long been used in agriculture as animal growth promotion agents. In fact, studies have shown that commercial meat products can be contaminated with streptogram-resistant organisms [9–11].

Resistance to the type B streptogramins can result from active efflux (Msr pumps), alteration of the target ribosome by methylation of the 23S rRNA (Erm methyl-transferases), and by the inactivating enzyme Vgb. Vgb was originally found in streptogramin-resistant *Staphylococcus aureus* [12] but has now been identified in other gram-positive bacteria such as *Enterococcus faecium* [13]. The enzyme was thought to be a hydrolse but has now been determined to be a lyase that linearizes the cyclic depsipeptide through a novel elimination reaction [14]. This reaction results in cleavage of the ester bond between the C terminus of the peptide and a secondary hydroxyl group derived from the Thr residue found at position 2 of the type B streptogramin peptide.

As the incidence of antibiotic resistance increases, there is a growing need for novel antibiotic compounds that can be used to treat infections.

SUMMARY OF THE INVENTION

The present invention addresses the need for novel antibiotics for use in humans and animals.

This vulnerable and invariant ester bond arises as a result of the action of a cyclizing thioesterase (TE) during nonribosomal peptide biosynthesis of the antibiotic [15]. We reasoned that isosteric replacement of this ester bond with a more stable amide could result in streptogramin analogs that were not susceptible to the action of Vgb. We report here the preparation and biological evaluation of chimeric streptogramin-tyrocidine peptides that are cyclized via amide rather than ester bonds and are impervious to inactivation by Vgb or methylation of the ribosome by Erm.

In one aspect of the invention, a novel antibiotic is provided. The novel antibiotic is a cyclic peptide antibiotic in which a linkage that is sensitive to a bacterial enzyme is replaced by a linkage that is resistant to cleavage by the bacterial enzyme.

In a preferred embodiment the cleavable bond is replaced with a stable bond such as an amide, a methylene bridge, N-methyl amide, enamine (—C=N—), or a sulfonamide bond.

In one preferred embodiment, the novel antibiotic is a cyclic peptide that comprises an amide bond between the C-terminal carboxyl group and an internal amine group.

In a preferred embodiment, the antibiotic comprises a Type B streptogramin-like structure in which the terminal carboxyl group is linked to an internal amine of a threonine mimic such as diaminopropionic acid via an amide bond.

The present invention also provides antibiotic compositions comprising the antibiotics of the present invention and a pharmaceutically acceptable carrier. The composition may include other therapeutic components such as a second antibiotic or an anti-inflammatory.

In another aspect of the invention, a method of rendering an antibiotic resistant to cleavage by an enzyme is provided. The method comprises replacing an enzyme sensitive linkage with a stable molecular bond while maintaining antibiotic activity.

In a preferred embodiment, an ester bond is replaced with a highly stable amide bond.

In a preferred embodiment, the antibiotic is resistant to cleavage by Vgb enzyme.

In another aspect of the invention, the antibiotic is chimeric in nature. The chimeric antibiotic comprises active fragments from two different antibiotics. Typically the two fragments will provide different mechanisms of action the first active fragment having a first activity and the second active fragment having a second activity.

In one embodiment, the active fragments provide an overall antibacterial activity that is equal to the sum of the activities of the two active fragments.

In another embodiment, the two active fragments act synergistically to provide a cumulative antibacterial effect in excess of the sum of the activities of the fragments.

In yet another embodiment, an antibiotic is provided that comprises two antibacterial fragments and has an antibacterial mechanism of action that is different from that of either of the component active fragments. It is clearly apparent that while the discussion has focused on two active fragments, a chimeric antibody that has three or more active fragments is also encompassed within the invention.

In a preferred embodiment, the antibiotic is selected from the group consisting of:

5

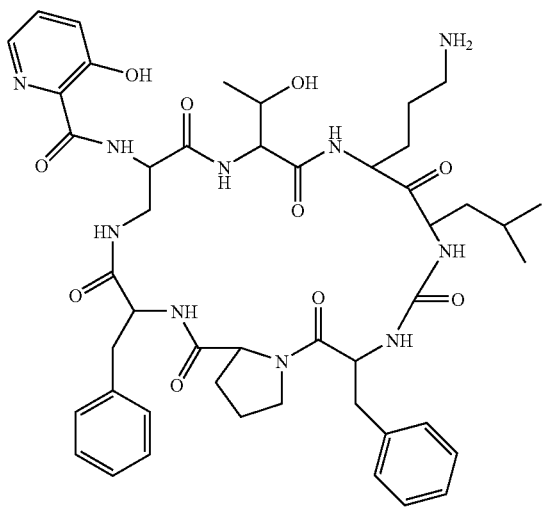

6

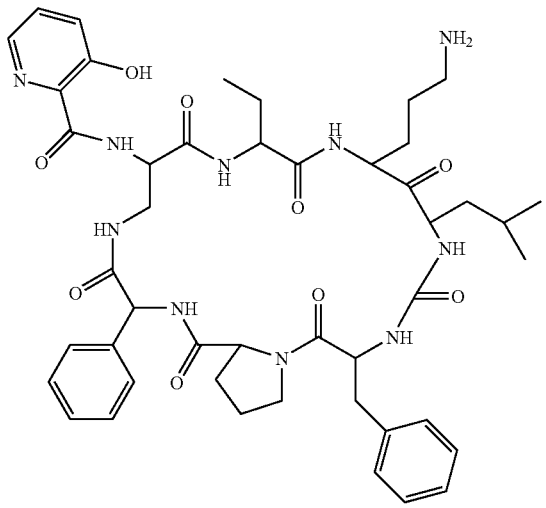

7

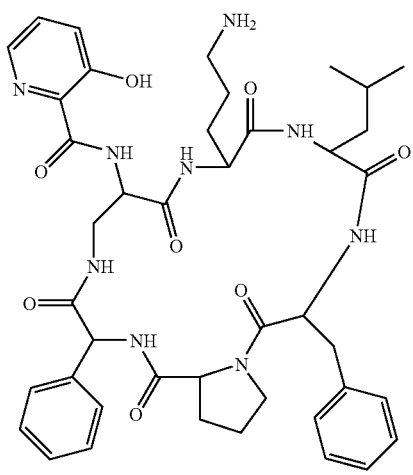

-continued

8

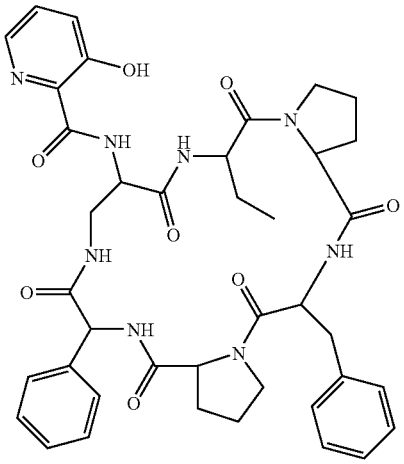

The present invention also provides methods and compositions for the prevention and treatment of microbial diseases in animal and human subjects. The method comprises administering to the subject an effective amount of an antibiotic of the present invention.

The antibiotics of the present invention are also useful in aquaculture to prevent and/or treat infections and promote growth.

In another aspect, an animal feed composition is provided which comprises the antibiotics of the present invention. The novel antibiotics can be added to animal feed to promote growth and/or prevent infection.

Methods for disinfecting surfaces such as surgical equipment, medical devices and food preparation equipment are also provided. The term surface also encompasses the skin surface. The methods of the present invention comprise contacting the surface to be disinfected with an effective amount of an antibiotic of the present invention.

BRIEF DESCRIPTION OF THE DRAWINGS

Preferred embodiments of the invention are described below with reference to the drawings wherein.

DETAILED DESCRIPTION

Figure 1:
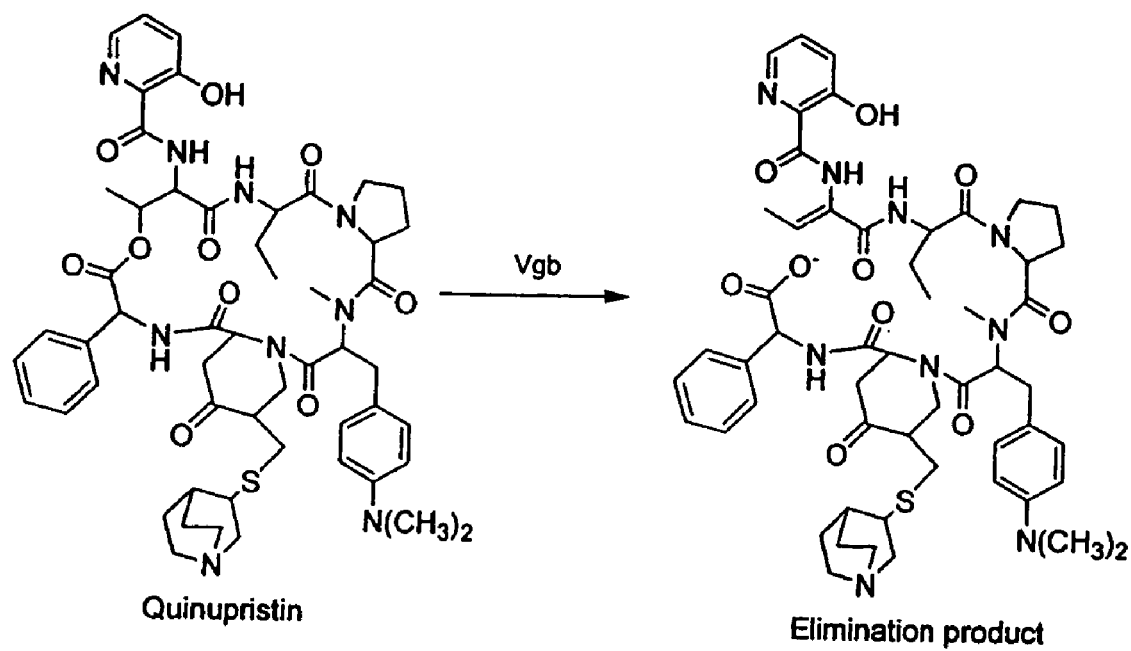
FIG. 1 demonstrates the mechanism whereby resistance to Type B streptogramin antibiotics occurs.

A wide variety of antibiotics have been used to combat bacterial infection and the incidence of antibiotic resistant organisms continues to grow. There is therefore a need for new antibiotics to treat infections caused by resistant microorganisms.

This invention relates to a novel antibiotic product. Cyclic peptide antibiotic derivatives as well as methods for their preparation and use are provided. As used herein "cyclic peptide antibiotic analogue or derivative" refers to a cyclic peptide which demonstrates antimicrobial activity. Cyclic peptide antibiotic derivatives that are effective against antibiotic-resistant bacteria are provided.

The novel antibiotic product comprises a modified antibiotic analogue that is resistant to cleavage by an enzyme that is capable of cleaving the unmodified antibiotic. An enzyme-sensitive bond is replaced by an enzyme-resistant bond. For example, an enzyme sensitive bond such as an ester bond may be replaced by an enzyme-resistant bond such as an amide bond, a methylene bridge, an N-methyl amide bond, an enamine bond or a sulfonamide bond. In one aspect of the invention, type B streptogramin antibiotic derivatives are provided.

The antibiotic derivatives of the present invention are useful in the prevention and treatment of microbial infection. The antibiotic derivative may be provided in a formulation composition for administration in a variety of ways. The antibiotic composition can be administered by a repeated dosing of immediate release dosage forms or as a controlled release formulation. The antibiotic product may be formulated in a way that is suitable for oral administration, parenteral injection, topical administration, administration in the eye or the ear, rectal or vaginal administration, as nose drops or by inhalation. In a preferred embodiment, the antibiotic product is formulated in a manner such that it is suitable for oral administration or for parenteral administration. For topical administration, the antibiotic may be provided in a composition that is formulated as an oil-in-water emulsion, or a water-in-oil emulsion as a lotion, cream, gel or ointment. The antibiotic of the present invention may also be provided in the form of a patch or the antibiotic composition may be formulated for use in the eye or ear or nose as a liquid emulsion. The antibiotic composition may also be formulated for rectal or vaginal administration in the form of a cream or emulsion, or other dissolvable dosage form similar to those used for topical administration. The antibiotic composition can be formulated for use in inhalation therapy by micronizing particles for inhalation.

Methods for treating and/or preventing microbial infections are also provided. One method comprises administering to an animal in need of such treatment a pharmaceutically effective amount of a pharmaceutical composition of the invention. As used herein, the term "animal" encompasses humans. The pharmaceutical compositions of the invention can be used to treat infections by gram-positive bacteria, gram-negative bacteria, protozoa, and mycoplasma.

The antibiotic composition of the present invention may be administered to a subject in need thereof by any of the following routes of administration: sublingual, transmucosal, transdermal, parenteral, etc., and preferably is administered orally or parenterally. The composition includes a therapeutically effective amount of the antibiotic. The dosage to be administered will vary according to the activity of the specific antibiotic, the disease or infection to be treated, the dosing schedule (i.e. how many pills/day) and the age, weight and health of the subject.

The antibiotic derivatives of the invention are also useful in aquaculture. There is a significant risk of microbial infection of an entire population in both small aquariums or ponds containing ornamental fish and the much larger tanks of fish farming operations. In aquaculture, the economic consequences of microbial disease are significant. Aquatic animals kept in tanks are also susceptible to bacterial infections. The widespread over-use of antibiotics in the fish-rearing industry has selected for highly resistant strains of bacteria that no longer respond to conventional antibiotic therapy.

The antibiotic derivatives of the present invention are used to prevent or treat infection in fish and aquatic animals. In one method of treating a microbial infection, the antibiotic derivative is injected directly into the muscle or blood stream of a fish or aquatic animal. This method is most effective for the larger fish species and breeds such as koi, and goldfish, and farmed species such as catfish, salmon, and trout. Alternatively, the antibiotic derivatives can be added to fish feed. This method is most effective for the treatment of internal systemic infections. The antibiotic derivatives can also be incorporated in bath or dip treatments. This method is particularly effective for treating surface infections of fish as fin rot, bacterial gill disease, or columnaris, and lesions, such as skin ulcers.

The antibiotic derivatives of the present invention are also useful as additives for animal/feed. The antibiotic derivative can be formulated in an animal feed premix or animal feed supplement containing the antibiotic and an edible carrier or diluent. These premixes or animal feed supplements may then be mixed with a sufficient quantity of an appropriate animal feed (e.g., livestock, poultry, fish, pet and/or other animal feed) to provide a final animal feed formulation having the desired level of the antibiotic derivative in the feed.

Preferred antibiotic products of the present invention are streptogramin derivatives, particularly Type B streptogramin derivatives.

Type B streptogramin antibiotics are peptides that are normally cyclized via an ester bond between the C-terminal carboxyl group and a hydroxyl group of a threonine residue. The antibiotic activity of the molecule is dependant upon cyclization. One of the mechanisms of resistance to the B class of streptogramins involves disrupting the cyclic structure. This occurs when an enzyme cleaves the molecule at the ester bond. The enzyme was thought to be a hydrolase but has now been determined to be a lyase, such as Vgb from *Staphylococcus aureus*, which linearizes the cyclic depsipeptide through a novel elimination reaction. This reaction is shown schematically in FIG. 1. The reaction results in cleavage of the ester bond between the C-terminus of the peptide and a secondary hydroxyl group derived from the Thr residue found at position 2 of the type B streptogramin peptide.

The vulnerable ester bond is formed as a result of the action of a cyclizing thioesterase associated with nonribosomal peptide synthesis of the antibiotic. The present invention demonstrates that isosteric replacement of this ester bond provides streptogramin analogues that are not susceptible to the action of Vgb.

Figure 2:
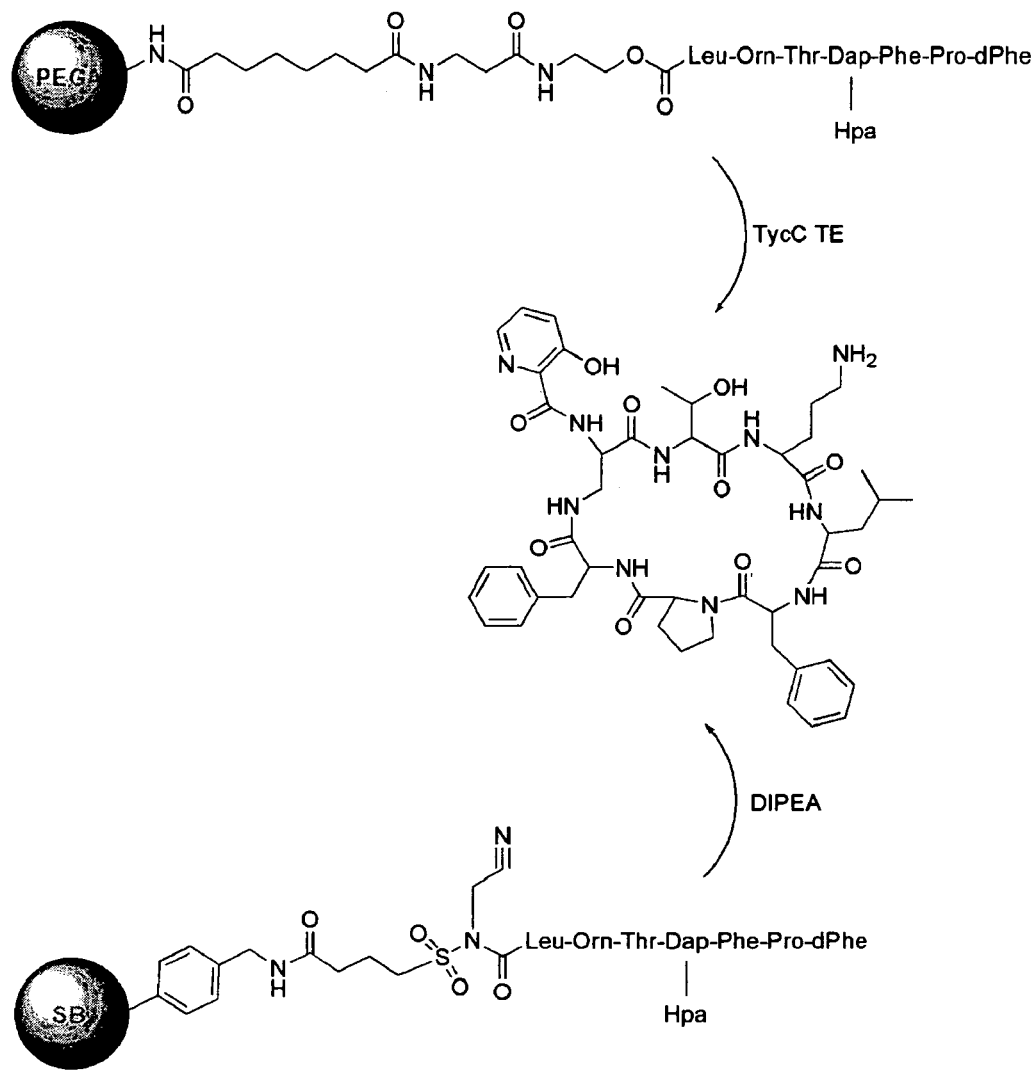
FIG. 2 illustrates schematically the strategies used to synthesize the peptides of the present invention.

Replacement of the ester linkage between the C-terminal carboxyl and side chain alcohol derived from Thr at position 2 with the more thermodynamically stable amide functionality results in type B streptogramins that were not substrates for the Vgb lyase. Peptides were synthesized using two solid phase strategies: a biomimetic approach using on-bead enzyme catalyzed cyclization and a chemical method using base-assisted cyclization as illustrated in FIG. 2. Further guidance regarding the synthesis can be found in Example 2 below.

Macrocyclic antibiotics are biosynthesized by polyketide synthetases and nonribosomal peptide synthetases. Prior to cyclization, these antibiotics are tethered to carrier proteins and a cognate thioesterase catalyses their release and cyclization if appropriate. Solid phase peptide synthesis on PEGA resin and recombinant tyrocidine thioesterase (TycC TE), provides an efficient route for the synthesis of cyclic peptide antibiotics [16, 17]. The TycC TE possesses the ability to cyclize a variety of tyrocidine analogs varying in length and functional groups [18, 19].

Figure 3:
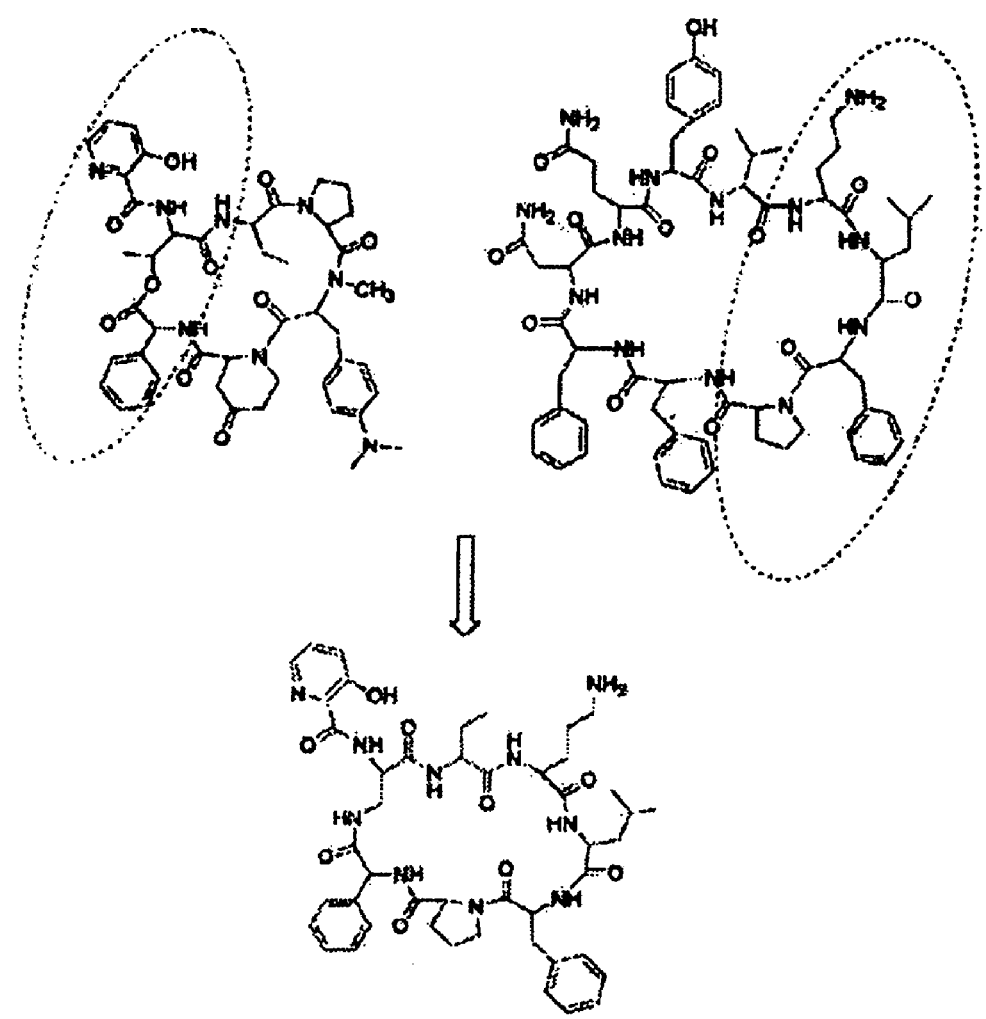
FIG. 3 illustrates the formation of a streptogramin-tyrocidine chimeric anti-microbial peptide.

FIG. 3 illustrates an example of how a streptogramin-tyrocidine chimeric antimicrobial peptide can be formed.

Streptogramin-like peptides that incorporate amide rather than ester bonds are provided. It is clearly apparent that replacement of the sensitive ester bond with any other type of bond that is resistant to a bacterial enzyme would also be effective and such derivatives are included within the scope of the invention. It is also clearly apparent that other types of antibiotics that have a vulnerable ester bond can be modified in the same manner to replace the ester bond with a more stable bond.

Several cyclic peptides were prepared using the strategy outlined in FIG. 2 and discussed further in Example 2 below. It is clearly apparent that other strategies could also be used to obtain cyclic peptides and this scheme is provided for exemplary purposes. In the scheme illustrated in FIG. 2, the peptides were synthesized using two solid phase strategies: a biomimetic approach using on-bead enzyme catalyzed cyclization (a) and a chemical method using base dependent cyclization (b).

This strategy was used to synthesize cyclic Type B-like peptides. The peptides were designed based on a knowledge of type B streptogramin structures, as summarized in Table 1, and the steric restrictions with respect to amino acids in a peptide that allow TE to function efficiently.

Since type B streptogramins occur both as hepta- and hexadepsipeptides, both lengths were investigated in the streptogramin analogues.

Figure 4:
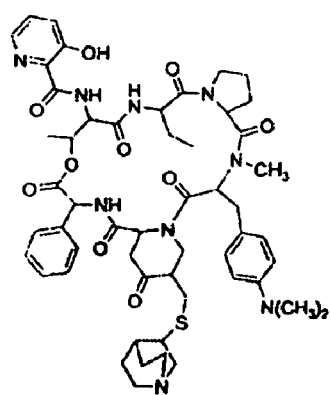
FIG. 4 illustrates the structures of exemplary antimicrobial peptides.
Figure 4:
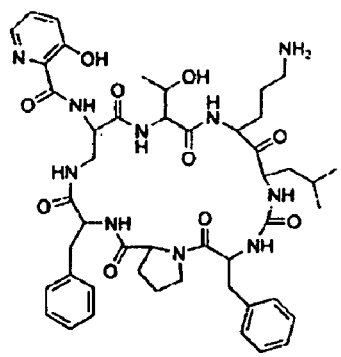
Figure 4:
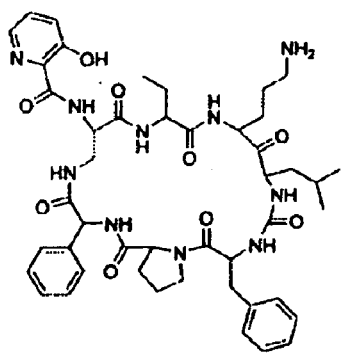
Figure 4:
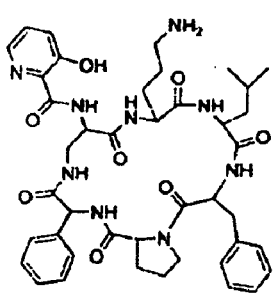
Figure 4:
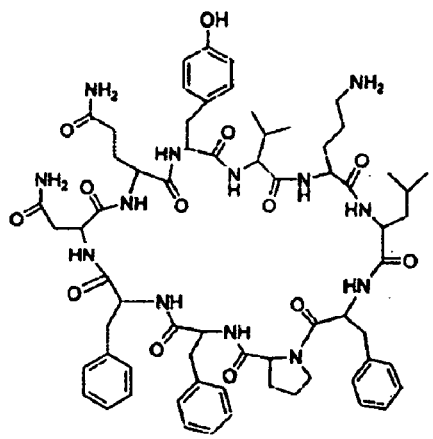
Figure 4:
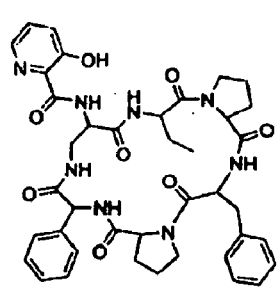

FIG. 4 illustrates the structures of some exemplary antimicrobial peptides that were synthesized and used to demonstrate the utility of the invention.

The antibacterial efficacies of the streptogramin analogues were assessed. The results of representative experiments are shown in Tables 2 and 3. The assays and the results are further discussed in Example 3. The results indicate that the analogues of the present invention are highly effective antibiotics.

To further demonstrate the resistance of the bond to cleavage by Vgb, the minimum inhibitory concentration for one exemplary compound, compound 5, was compared to that of a known antibiotic, quinupristin, in the absence of Vgb and was shown to be comparable. When Vgb was present, the MIC increased significantly for quinupristin but remained the same for Compound 5, demonstrating the stability of the bond. The results are shown in Table 3 and the experiment is described in greater detail in Example 3 below.

The present invention provides a method for synthesis of chimeric peptides comprising the following steps:

Chemical Synthesis:
1. Attachment of the first amino acid to sulfamylbutyryl resin;
2. Deprotection of the amino terminal using piperidine in dimethylformamide;
3. Repeat steps 1 and 2 until the last amino acid is attached and deprotected;
4. Activation of the resin using iodoacetonitrile;
5. Cyclization using diisopropylethylamine as a base.
6. Purification of antibiotic using preparative HPLC.

Chemo-Enzymatic Synthesis:
1. Attachment of a linker, consisting of suberic acid, beta-alanine and ethanolamine to PEGA resin.
2. Attachment of the first amino acid;
3. Deprotection of the amino terminal using piperidine in dimethylformamide;
4. Repeat steps 2 and 3 until the last amino acid is attached and deprotected;
5. Cyclization using Tyrocidine thioesterase (Tyc TE)
6. Purification of antibiotic using preparative HPLC.

Novel antibiotics prepared according to the method of the invention are provided. The antibiotics of the present invention exhibit anti-microbial activities and they are not susceptible to known antibiotic resistance mechanisms, such as Vgb hydrolysis and other established mechanisms.

The chimeric antibiotics of the present invention retain the active fragments of two natural products. Depending on the specific combination of active fragments, a chimeric cyclic peptide antibiotic of the present invention may demonstrate the functional antibacterial mechanism of action of one of the parent molecules, both of the parent molecules or a novel antibacterial mechanism separate from the activities of the parent compounds. Compound 5 illustrates that a new, previously unrecognized biological interaction can be uncovered by combining the active portions of two compounds. Although compound 5 was based on two active fragments, it is apparent to one skilled in the art that if two active fragments can result in discovery of a new functionality, then a combination of three three or more active fragments could also provide insight into novel functionalities. Based on this reasoning, the present invention provides novel antibiotics incorporating two or more active fragments.

The present invention also provides a novel method of drug discovery. By combining organic synthesis, molecular engineering and natural product chemistry enzymes can be used to select for novel compounds that function according to previously unknown mechanisms of action.

The present invention provides a novel class of antibiotics in which an enzyme sensitive bond is replaced by an enzyme resistant bond. These antibiotics are able to counteract the antibiotic resistance mechanisms of bacteria that are based on enzymatic cleavage.

The present invention also provides a novel class of antibiotics that are chimeras, containing fragments of two or more antibiotics. These chimeric antibodies counteract bacterial antibiotic resistance mechanisms by interfering with known resistance mechanisms. For example, they may eliminate susceptibility to Vgb hydrolysis or Erm methyltransferases or they may not be active in disrupting cell membranes. Alternatively, they may provide their antimicrobial activities through novel mechanisms of action not normally associated with a parent moiety. These antibiotics provide powerful tools for identifying antimicrobial targets.

The rampant increase in the number of antibiotic resistant organisms has placed great pressure on the pharmaceutical, medical, and academic organizations to gain a better understanding of the mechanism of resistance, and to develop new antimicrobials that can be used to combat these organisms. The present invention demonstrates that a chemoenzymatic approach using TycC TE can be used to generate novel, cyclic, antibiotics. Significant yields can be obtained through synthesis of a precursor to a streptogramin analogue solid phase support followed by cyclization using DIPEA. The present invention demonstrates the synthesis of novel antibiotic analogues that are able to resist the antibiotic resistance mechanisms of pathogens. The analogues of the present invention demonstrate antibacterial mechanisms that may be equivalent to the parent antibiotic(s) or they may demonstrate novel mechanisms of action. The present invention provides a new class of antibiotics designed to evade inactivation by their resistance enzyme counterparts, and provides a means of combating the rise in antibiotic resistant organisms.

The above disclosure generally describes the present invention. It is believed that one of ordinary skill in the art can, using the preceding description, make and use the compositions and practice the methods of the present invention. A more complete understanding can be obtained by reference to the following specific examples. These examples are described solely to illustrate preferred embodiments of the present invention and are not intended to limit the scope of the invention. Changes in form and substitution of equivalents are contemplated as circumstances may suggest or render expedient. Other generic configurations will be apparent to one skilled in the art. All journal articles and other documents such as patents or patent applications referred to herein are hereby incorporated by reference.

EXAMPLES

Although specific terms have been used in these examples, such terms are intended in a descriptive sense and not for purposes of limitation. Methods of molecular biology and chemistry referred to but not explicitly described in the disclosure and these examples are reported in the scientific literature and are well known to those skilled in the art.

Example 1

Reagents and General Techniques

PEGA-$NH_2$ and sulfamylbutyryl resins, and all Fmoc and Boc-protected amino acids, except Fmoc-dAbu-OH, were purchased from Novabiochem. Recombinant Vgb from *S. aureus* and truncated tyrocidine thioesterase (Tyc C) were expressed and purified as previously described (16, 23). LC/MS was conducted on a Micromass Quatro LC by Dr. K. Green at the McMaster Regional Centre for Mass Spectrometry.

Example 2

Synthesis of Peptides

Solid Phase Synthesis

PEGA-NH2 and sulfamylbutyryl resins, and all Fmoc and Boc-protected amino acids, except Fmoc-dAbu-OH, were purchased from Novabiochem. Recombinant Vgb from *Staphylococcus aureus* and truncated tyrocidine thioesterase (TycC TE) were expressed and purified as previously described [14, 20]. LC/MS was conducted on a Micromass Quatro LC by Dr. K. Green at the McMaster Regional Centre for Mass Spectrometry.

Two solid-phase strategies were used to achieve the synthesis of cyclic peoptides. The first was recently described biomimetic approach on PEGA-NH2 resin that uses a CoA-mimicking linker followed by sequential attachment of the Fmoc-protected amino acids and enzymatic cyclization [17]. In the second approach, standard Fmoc-amino acids were loaded on sulfamylbutyryl resin. FIG. 4 illustrates the structures of exemplary antimicrobial peptides synthesised and assayed.

The general synthesis of the linear peptides followed the following procedure: to the resin loaded with the first amino acid (1 g) was added 10 ml of 20% piperidine in dimethylformamide (DMF) solution, followed by agitation for 20 min and wash cycles of DMF (3×10 ml), iso-propanol (3×10 ml), and DMF (2×10 ml). Subsequently, a freshly prepared mixture of the Fmoc-protected amino acid (Fmoc-AA-OH) (5 eq), 1-hydroxybenzotriazole (5 eq), PyBop (5 eq), and diisopropylethylamine (diPEA) (10 eq) in DMF (5 ml) was added and the reaction mixture was agitated for 2 to 4 hrs. The washing cycle was repeated and the resulting resin was subjected to Kaiser test [29] to assess the efficiency of coupling. If the test was positive, the coupling was repeated until a negative test result was obtained. Otherwise, the synthesis proceeded to the next round of deprotection and coupling. Following the coupling of the last amino acid to the resin, the protected peptide was treated with 10 ml of trifluoracetic acid (TFA)/water/triisopropylsilane (TIPS) (9.5:0.25:0.25) for 2 hr at room temperature and wash sequentially with DMF, iso-propanol, and methanol and dried over KOH under vacuum for 4 hr.

TycC TE Catalyzed Peptide Cyclization

Purified recombinant TycC TE was added to 200–500 mg of deprotected peptide on PEGA resin as described in [17] for 30 min. The mixture was then filtered and the process repeated. The resin was subsequently washed twice with acetonitrile and the soluble fractions pooled, lyophilized, and analyzed by LC/MS.

Base-Promoted, On-Resin Peptide Cyclization

On-resin cyclization of the linear peptide precursor was carried out by immersing the resin in 2% DiPEA in THF (200 ml) for 16 hr at room temperature [25]. After filtration the solvent was removed in vacuo, the crude product was resuspended in 50% acetonitrile/water, and the solution lyophilized. The final product was characterized by LC-MS analysis and purified by preparative reverse phase HPLC (Vydac 218TP1022 column).

Synthesis of Peptides on Sulfamylbutyryl Resin

Peptide 5 was synthesized on sulfamylbutyryl resin (1 g) following the general procedure described above. 3-Hydroxypicolinic acid (3-Hpa) was the last amino acid to be incorporated in the peptide chain after trityl group deprotection of diaminopropionic acid with a mixture of 3% TFA, 5% TIPS, and 92% DCM (10 ml) for 2 hr at room temperature. A the end of the hpeoptide synthesis, the resin was activated with iodoacetonitrile as already described [30]. Bocdeprotection was carried out using a mixture of TFA/phenol/TIPS/water (78.8:0.5:0.5:0.2) (10 ml) for 2 hr at room temperature. The cycliztaion reaction was carried out as desccribed above and the peptide product purified by reverse phase HPLC in an overall yield of 10 mg (1.3%).

600 MHz, $^1$H-NMR spectra data for 5 in 60:40 $CD_3CN$: D2O, δ ppm, J in Hz: 0.78 (d, 3H, J 6.5); 0.83 (d, 3H, J 6.5); 1.12 (d, 3H, J 3.8); 1.21–1.27 (m, 1H); 1.33–1.39 (m, 1H); 1.41–1.49 (m, 2H); 1.63–1.77 (m, 8H); 1.81–1.83 (m, 1H); 2.78–2.82 (m, 4H); 2.84–298 (m, 1H); 3.06–3.10 (m, 4H); 3.46–3.50 (m, 2H); 3.57–3.61 (m, 2H); 3.64–3.68 (m, 2H); 4.15–4.17 (m, 1H); 4.21–4.23 (m, 1H); 4.25–4.30 (m, 1H); 4.33–4.41 (m, 1H); 4.64–4.68 (m, 1H); 4.73–4.75 (t, 1H, $J_1$ 5.2, $J_2$ 5.2); 7.06–7.29 (m, 10H); 7.37–7.39 (d, 1H, J 8.5); 7.47–7.50 (m, 1H); 7.57–7.61 (m, 1H); 7.83–7.85 (t, 1H, $J_1$ 6.1, $J_2$ 5.9); 7.89–793 (m, 2H).

$^{13}$C NMR: 18.62, 19.88, 22.64, 22.69, 24.07–24.13, 25.38, 29.04, 29.89, 36.36, 37.32, 39.61, 41.04–41.17, 48.02, 59.91, 54.25–54.48, 56.29, 59.83, 61.15, 67.32, 127.78, 128.10, 129.43–129.51, 130.13–130.26, 136.92, 138.21, 158.40, 162.41, 168.75, 172.31–172.47, 173.30–173.41, 173.95, 174.51.

TOF MS ES+ m/z 927.4754 ([M+H]+, calculated m/z for $C_{47}H_{62}N_{10}O_{10}$, 926.4650).

The patricin analog 8 was synthesized using the same solid phase strategy as for the synthesis of peptide 5. The cyclized product was purified using reverse phase HPLC.

700 MHz, $^1$H-NMR spectra data for 8 in 60:40 $CD_3CN$:$D_2O$, δ ppm, J in Hz.

0.86 (t, 3H, $J_2$ 3.8, $J_2$ 3.6); 1.66–1.72 (m, 2H); 1.85–1.95 (m, 4H); 2.05–2.15 (m, 4H); 2.80–2.91 (m, 2H); 3.06–3.21 (dd, 2H); 3.38–3.53 (m, 4H); 3.56–3.62 (m, 2H); 3.67–3.74 (m, 2H); 4.15–4.20 (m, 1H); 4.25–4.29 (m, 1H); 4.30–4.38 (m, 2H); 4.81–4.84 (m, 1H); 4.85 (d, 1H, J 7.1); 5.13–5.20 (m, 1H); 7.09–7.11 (m, 4H); 7.13–7.55 (m, 6H); 7.61–7.71 (m, 2H); 8.18–8.21; and 8.57–8.59 (m, 1H).

$^{13}$C NMR: 10.24, 23.87, 24.22, 26.25, 29.24, 30.20, 37.64, 48.47, 51.16, 53.16, 53.24, 55.63, 60.26, 61.60, 61.89, 119.31, 127.34, 127.88, 129.25, 129.53, 129.64, 129.95, 130.27, 130.48, 132.02, 137.10, 138.00, 141.64, 158.15, 170.33, 172.13, 172.26, 173.35, 173.87, and 174.59.

MS ES+ m/z 767.8 [M+H]+, calculated m/z for $C_{40}H_{46}N_8O_8$) 766.8.

Results

It was determinted that critical residues required for efficient cyclization via TycC TE were D-Phe$^1$ and L-Orn$^9$. Changing L-Leu$^{10}$ did not abolish cyclization; however a 4-fold decrease in $k_{cat}$ was detected. The synthesis of cyclic tyrocidine analogs with properties and constituents of type B streptogramin peptides is provided. This approach is shown schematically in FIG. 3.

The chimeric peptides were based on the diversity of type B streptogramin chemical structures (summarized in Table 1), knowledge of the important contact points of streptogramin B with the ribosome [7], and the steric constraints for TycC TE established in [20]. Since type B streptogramins occur both as cyclic hexa- and heptadepsipeptides (not counting the extracyclic 3-Hpa group), both lengths were synthesized. The hexadepsipeptides 1–4, the heptapeptides 5 and 6, and the hexapeptide 7 as described in Table 1 were initially prepared on PEGA resin and cyclized using the recombinant TycC TE.

Incubation of TycC TE with the resin-bound linear precursors resulted in cyclization of these peptides as determined by LC-MS. This indicated that TycC TE was not only capable of cyclizing tyrocidine analogs, but was also capable of cyclizing the designed tyrocidine-streptogramin chimeras. Partially purified material from these reactions was used to test their antibiotic properties in disk diffusion susceptibility assays using *E. coli* BAS901. This strain is deficient in the Imp/OstA outer membrane protein, which is involved in cell envelope biogenesis [21, 22] and as a result exhibits increased outer membrane permeability and susceptibility to antibiotics, and increased susceptibility toward organic solvents [23, 24]. The results of this assay, shown in Table 2, showed that compounds 5, 6, and 7 blocked cell growth, and importantly that these compounds retained antibacterial activity even in the presence of the streptogramin inactivating enzyme Vgb.

To improve the yield of chimeric antibiotics, a modified version of a nonenzymatic method recently reported by Qin et al. [25] for the cyclization of tyrocidine was used. Modifying this approach, 10 mg of purified cyclic compound 5 was obtained and its structure confirmed via $^1$H, $^{13}$C-NMR and mass spectrometry. Compound 5 was used as an exemplary compound since initial results as reported in Table 2 indicated that 5, 6, and 7 were comparably active.

Example 3

Antibacterial Properties of Synthesised Compounds

*E. coli*-Expressing Streptogramin B Resistance Elements

A hyperpermeable *E. coli* strain, *E. coli* BAS901, harboring a plasmid constitutively expressing Vgb was created for in vivo studies. The plasmids pVGB, described previously in [14], and pUC109 were digested with XbaI and BamHI, to yield an approximately 1 kb fragment containing a ribosomal binding site upstream of vgb, and linearized pUC19 backbone, respectively. The vgb fragment was then subcloned into the linearized pUC19 backbone downstream of pLac yielding pUC19-VGB. Both pUC19-VGB and pUC19 were transformed *E. coli* BAS901.

In order to test the effects of 5 against *E. coli* BAS901 harboring ermB, the 23S rRNA methyltransferase, the plasmid pJIM2246 ΩermB [13] was purified from *Staphylococcus aureus* RN4220/pJIM2246 ΩermB. ErmB was subsequently amplified from pJIM2246 ΩermB via polymerase chain reaction using primers 5'-GAATTCCATATGAAC-AAAAATATAAAATATTCTCAAAAC AND 5'-GAATT-CGGATCCTCATAGAATTAATTTCCTCCCG (engineered restriction enzyme sites are underlined). The amplified product was subcloned into pCR4Blunt-TOPO (Invitrogen) and transformed into *E. coli* XL10 GOLD, resulting in ermB being positioned in frame with the lacZ gene. This construct, designated pTOPOerm, was then used as template in the reamplification of ermB using a new forward primer containing a strong ribosomal binding consensus sequence (shown in italics); 5-A*TCTAGAGGAGGAATTCCATATG*. The amplification product was again subcloned into pCR4Blunt-TOPO and transformed into XL10 GOLD, resulting in trhe construct pTOPOnewerm. PTOPOnewerm was digested with PstI and BamHI, and the resulting fragment contained ermB downstream of the ribosomal binding site. This fragment was ligated to pUC19 digested with the same restriction enzymes. The resulting construct, pUC19-ermB was subsequently transformed into *E. coli* BAS901.

Determination of Antibiotic Activity of Peptides

The antibiotic activity of the peptides synthesized in this study was initially assayed using a disk assay where samples were applied to sterile paper disks placed on a fresh lawn of bacterial culture on appropriate agar plates as required by the organism. These were then incubated for 16 hr at 37° C. and the zone of growth inhibition surrounding the disks recorded. For quantitative assessment of antibiotic activity in liquid culture, the minimal inhibitory concentration (MIC) of peptides was determined by serial dilution studies. The peptides and standard antibiotics were dissolved in DMSO and the final concentration of DMSO in the liquid cultures was 5%. Both *S. aureus* RN4220 and *E. coli* BAS901 were able to grow efficiently at this level of DMSO.

Crude material from the initial synthesis reactions was used to test the potential of the analogues as antibiotics in susceptibility assays where a solution of the compound was placed on a paper disk on a lawn of bacteria. As described above, *E. coli* BAS901 is deficient in the Imp/OstA protein, an outer membrane protein, involved in cell envelope biogenesis (1, 5). Strains deficient in this protein tend to exhibit increased outer membrane permeability and susceptibility to small molecules including antibiotics, and increased susceptibility towards organic solvents (3, 18). The antibiotic activity of the peptides synthesized in this study was initially assayed using a disk assay where samples were applied to sterile paper disks placed on a fresh lawn of bacterial culture on Tryptic Soya, Luria Broth, or Brain Heart Infusion Agar plates. These were then incubated for 16 hrs at 37° C. and the zone of growth inhibition surrounding the disks recorded.

Figure 5:
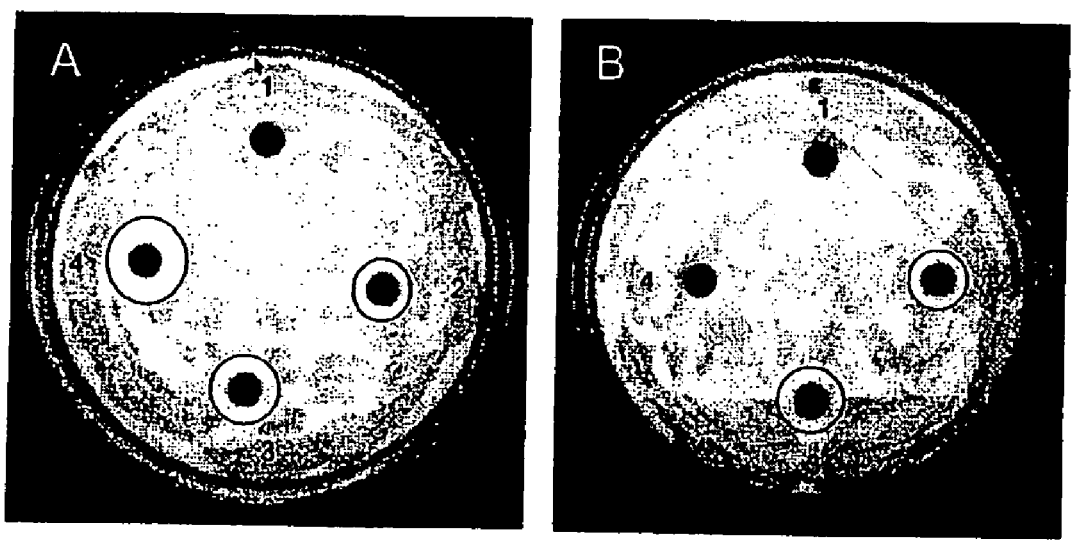
FIG. 5 illustrates the anti-microbial stability of the peptides in the presence of a lyase.

FIG. 5 depicts the results of application of crude COMPOUND 6 and COMPOUND 7 on *E. coli* BAS901/pUC19 and *E. coli* BAS901/pUC19-VGB. In panel A, it can be seen that quinupristin, COMPOUND 6, and COMPOUND 7 exhibit a zone of inhibition indicating that they possess antibacterial properties. COMPOUND 5 (not shown) also exhibited similar zones of inhibition to COMPOUND 6. In panel B however, Vgb is being constitutively expressed due to constitutive low-level expression via the lac promoter, and thus quinupristin is inactivated by the action of this enzyme. COMPOUND 5, COMPOUND 6, and COMPOUND 7 however, still exhibit zones of inhibition even in the presence of Vgb. This indicates that these peptides are novel, inactivation-proof streptogramin antibiotics. Table 2 also demonstrates inhibition of bacterial growth by several antibiotics.

On-resin chemical cyclization of 5 provided sufficient material for more extensive analysis of antibacterial activity and investigation of its ability to inhibit the streptogramin inactivating enzyme Vgb. This enzyme however was insensitive to 5 in concentrations of up to 0.4 mM. A previously synthesized, isosteric amide analog of the minimal Vgb substrate Hpa-Thr(Ophg)-Ome [14] was not an inhibitor of Vgb at concentration of up to 1 mM (unpublished). These observations suggest that the ester bond may be crucial for substrate binding within the active site of the enzyme, although this possibility awaits analysis of the 3D structure of the inactivating enzyme. Regardless of the actual mechanism, the design of these streptogramin-tyrocidine chimeras of the present invention result in antibiotics that are not recognized by a streptogramin inactivation enzyme.

In vivo antibacterial activity of 5 was further explored using a variety of gram-positive and gram-negative bacteria (Table 2). Compound 5 demonstrated growth inhibition activity against the hyperpermeable gram-negative bacterium *E. coli* BAS901, but not wild-type *E. coli* 25922 or other gram-negative bacteria including *Salmonella enterica* serovar *Typhimurium* and *Haemophilus influenzae*. On the other hand, 5 was active against the gram-positive bacteria *Bacillus subtilis, Enterococcus faecium, Enterococcus faecalis, Streptococcus pneumoniae, Staphylococcus epidermidis, Staphylococcus saprophyticus*, and *Micrococcus luteus*. Thus, the cyclic peptide analogs of the present invention have broad spectrum activity against important gram-positive human pathogens.

Comparison of the MIC values for quinupristin and 5 against control *E. coli* (BAS901/pUC19), *E. coli* expressing the streptogram inactivating enzyme Vgb (BAS901/pUC19VGB), and *E. coli* with the ribosome protecting enzyme Erm methyltransferase (BAS901/pUC19ermB) indicated that unlike quinupristin, the antibacterial effects of 5 are invariant in the presence of these resistance enzymes (Table 3). These results suggest that compound 5 was not a substrate for Vgb and that compound 5 is not susceptible to the target modification resistance afforded through ErmB-mediated methylation of the 23S rRNA of ribosome.

Quinupristin and dalfopristin act in a synergistic manner. Experiments to determine whether compound 5 could also synergise with dalfopristin were performed against both *B. subtilis* 1A752 and *E. coli* BAS901 in microtiter plates using a standard checker-board technique. The results suggest an additive, not synergistic, effect with dalfopristin Hemolysis Assay Human red blood cells were freshly harvested, washed with 0.85% saline solution with 5 mM EDTA and resuspended in the same solution to an $A_{412}$ of 0.6. The hemolysis assay was performed in 1.5 ml Eppendorf tubes with the addition of either 5 in DMSO, saline, gramicidin (final concentration 30 µg/ml), or DMSO (5% final), for both 3 and 9 hr at 37° C. with occasion gentle mixing. The mixtures were then centrifuged and the $A_{412}$ of the supernatant measured.

The hemolytic activity of compound 5 was compared with the commercially available, channel-forming antibiotic gramicidin S (tyrocidine is not commercially available). Compound 5 showed no significant hemolytic properties even after a 9 hr exposure, while gramicidin lysed cells rapidly under identical conditions (Supplemental Data). Consistent with the lack of membrane damaging activity was our observation that 5 is bacteriostatic and not bactericidal against *E. coli* BAS901 and *B. subtilis* 1A752.

These surprising results therefore indicate that the mode action of certain chimeric antibiotics do not always parallel either type B streptogramins or channel forming peptides. In an effort to further explore the impact of altering the ester bond of type B streptogramins, an analog of the antibiotic patricin A replacing the Thr-phenylglycine cyclizing ester with the diaminopropionic acid-phenylglycine amide (compound 8). This compound differs also from patricin A in the lack of N methylation between amino acid residues 4 and 5. Compound 8 showed no antibacterial activity nor did it inhibit in vitro translation (Table 2 and FIG. 6). The chimeric antibiotics of the present invention represent a new class of antimicrobial peptides.

In Vitro Translation Assay

Inhibition of translation was monitored using an Active-Pro In Vitro Translation Kit from Ambion. Briefly, a reaction mixture was prepared as per the manufacturer's instructions that contained all of the constituents necessary (including [$^{35}$S]-methionine) except for DNA template. These mixtures were then preincubated for 15 min at room temperature in the presence or absence of various antibiotics. Subsequent to the preincubation period, a control template containing a chloramphenicol acetyltransferase gene under control of a bacteriophage T7 promoter was added and the reaction carried out for 1 hr at 37° C. Due to the insoluble nature of some of the antibiotics, the final DMSO concentration in each reaction including controls was maintained at 5% (v/v). Aliquots were taken after 1 hr, and separated on SDS polyacrylamide gels. The efficiency of translation of $^{35}$S-labeled chloramphenicol was analyzed and quantified using a Typhoon 9200 variable mode imager (Image-Quant 5.2 software).

Figure 6:
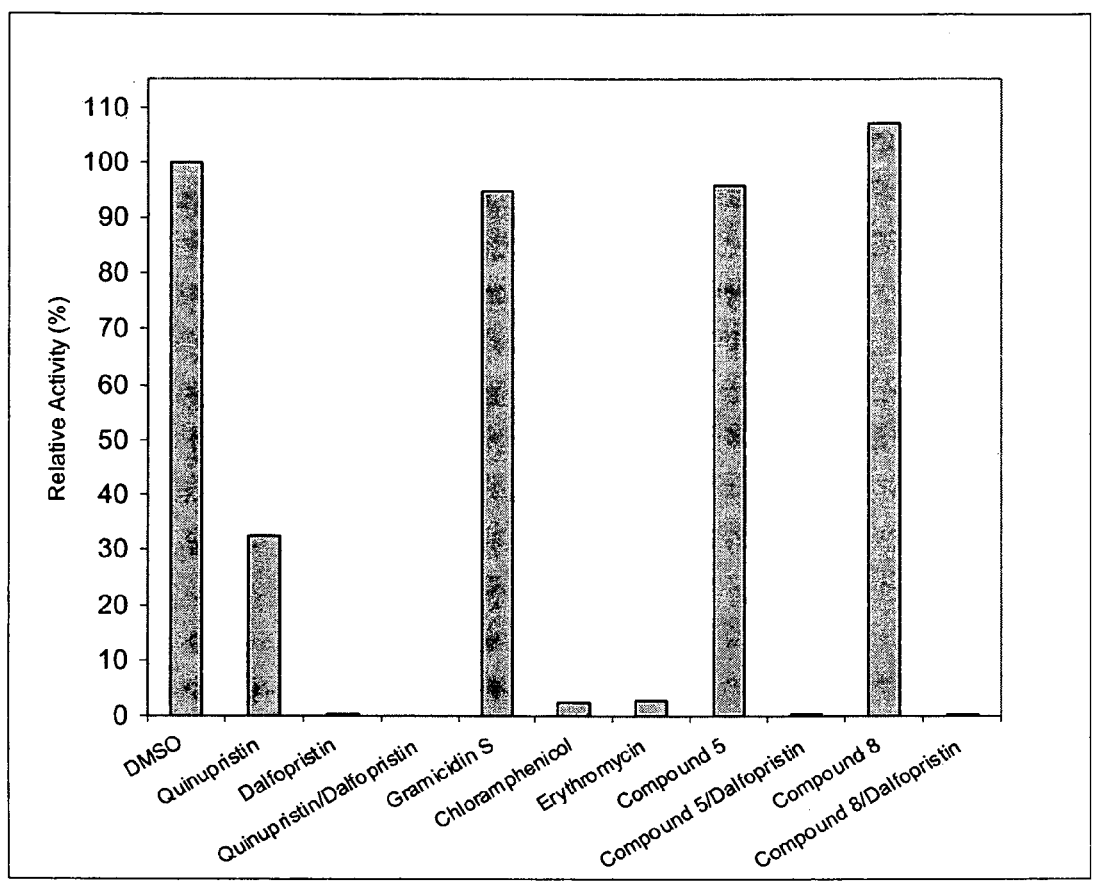
FIG. 6 illustrates graphically the impact of various antibiotics on in vitro translation.

To establish if that antimicrobial activity of 5 was the result of inhibition of translation, the impact of this compound on the fficiency of an in vitro translation system was assessed. While the known inhibitors of translation chloramphenicol, erythromycin, and the streptogramin dalfopristin and quinupristin did block in vitro translation, compound 5 did not at 250 µg/ml as shown in FIG. 6. Furthermore, fluorescence titration experiments with purified inact *E. coli* ribosomes that measures increase of the fluorescence associated with the Hpa moiety did support ribosome binding by quinupristin as previously shown [28], but compound 5 did not appear to interact with the ribosome in this study.

All references are incorporated herein by reference.

REFERENCES

1. Johnston, N. J., Mukhtar, T. A., and Wright, G. D. (2002). Streptogramin antibiotics: mode of action and resistance. Curr. Drug. Targets 3, 335–344.
2. Delgado, G., Jr., Neuhauser, M. M., Bearden, D. T., and Danziger, L. H. (2000). Quinupristin-dalfopristin: an overview. Pharmacotherapy 20, 1469–1485.
3. Eliopoulos, G. M. (2003). Quinupristin-dalfopristin and linezolid: evidence and opinion. Clin Infect Dis 36, 473–481.
4. Cocito, C. (1979). Antibiotics of the virginiamycin family, inhibitors which contain synergistic components. Microbiol. Rev. 43, 145–192.
5. Cocito, C., Di Giambattista, M., Nyssen, E., and Vannuffel, P. (1997). Inhibition of protein synthesis by streptogramins and related antibiotics. J. Antimicrob. Chemother. 39 Suppl A, 7–13.
6. Di Giambattista, M., Chinali, G., and Cocito, C. (1989). The molecular basis of the inhibitory activities of type A and type B synergimycins and related antibiotics on ribosomes. J. Antimicrob. Chemother. 24, 485–507.
7. Harms, J. M., Schluenzen, F., Fucini, P., Bartels, H., and Yonath, A. E. (2004). Alterations at the peptidyl transferase centre of the ribosome induced by the synergistic action of the streptogramins dalfopristin and quinupristin. BMC Biol 2, 4.
8. Jones, R. N., Farrell, D. J., and Morrissey, I. (2003). Quinupristin-dalfopristin resistance in *Streptococcus pneumoniae*: novel L22 ribosomal protein mutation in two clinical isolates from the SENTRY antimicrobial surveillance program. Antimicrob Agents Chemother 47, 2696–2698.
9. Simjee, S., White, D. G., Meng, J., Wagner, D. D., Qaiyumi, S., Zhao, S., Hayes, J. R., and McDermott, P. F. (2002). Prevalence of streptogramin resistance genes among *Enterococcus* isolates recovered from retail meats in the Greater Washington D.C. area. J Antimicrob Chemother 50, 877–882.
10. Simjee, S., White, D. G., Wagner, D. D., Meng, J., Qaiyumi, S., Zhao, S., and McDermott, P. F. (2002). Identification of vat(E) in *Enterococcus faecalis* isolates from retail poultry and its transferability to *Enterococcus faecium*. Antimicrob Agents Chemother 46, 3823–3828.
11. Soltani, M., Beighton, D., Philpott-Howard, J., and Woodford, N. (2000). Mechanisms of resistance to quinupristin-dalfopristin among isolates of *Enterococcus faecium* from animals, raw meat, and hospital patients in Western Europe. Antimicrob Agents Chemother 44, 433–436.
12. Allignet, J., Aubert, S., Morvan, A., and el Solh, N. (1996). Distribution of genes encoding resistance to streptogramin A and related compounds among staphylococci resistant to these antibiotics. Antimicrob. Agents Chemother. 40, 2523–2528.
13. Bozdogan, B., and Leclercq, R. (1999). Effects of genes encoding resistance to streptogramins A and B on the activity of quinupristin-dalfopristin against *Enterococcus faecium*. Antimicrob. Agents Chemother. 43, 2720–2725.
14. Mukhtar, T. A., Koteva, K. P., Hughes, D. W., and Wright, G. D. (2001). Vgb from *Staphylococcus aureus* Inactivates Streptogramin B Antibiotics by an Elimination Mechanism Not Hydrolysis. Biochemistry 40, 8877–8886.
15. de Crecy-Lagard, V., Saurin, W., Thibaut, D., Gil, P., Naudin, L., Crouzet, J., and Blanc, V. (1997). Streptogramin B biosynthesis in *Streptomyces pristinaespiralis* and *Streptomyces virginiae*: molecular characterization of the last structural peptide synthetase gene. Antimicrob Agents Chemother 41, 1904–1909.
16. Kohli, R. M., Takagi, J., and Walsh, C. T. (2002). The thioesterase domain from a nonribosomal peptide synthetase as a cyclization catalyst for integrin binding peptides. Proc Natl Acad Sci USA 99, 1247–1252.
17. Kohli, R. M., Walsh, C. T., and Burkart, M. D. (2002). Biomimetic synthesis and optimization of cyclic peptide antibiotics. Nature 418, 658–661.
18. Kohli, R. M., Trauger, J. W., Schwarzer, D., Marahiel, M. A., and Walsh, C. T. (2001). Generality of peptide cyclization catalyzed by isolated thioesterase domains of nonribosomal peptide synthetases. Biochemistry 40, 7099–7108.
19. Trauger, J. W., Kohli, R. M., and Walsh, C. T. (2001). Cyclization of backbone-substituted peptides catalyzed by the thioesterase domain from the tyrocidine nonribosomal peptide synthetase. Biochemistry 40, 7092–7098.
20. Trauger, J. W., Kohli, R. M., Mootz, H. D., Marahiel, M. A., and Walsh, C. T. (2000). Peptide cyclization catalysed by the thioesterase domain of tyrocidine synthetase. Nature 407, 215–218.
21. Braun, M., and Silhavy, T. J. (2002). Imp/OstA is required for cell envelope biogenesis in *Escherichia coli*. Mol Microbiol 45, 1289–1302.
22. Abe, S., Okutsu, T., Nakajima, H., Kakuda, N., Ohtsu, I., and Aono, R. (2003). n-Hexane sensitivity of *Escherichia coli* due to low expression of imp/ostA encoding an 87 kDa minor protein associated with the outer membrane. Microbiology 149, 1265–1273.
23. Sampson, B. A., Misra, R., and Benson, S. A. (1989). Identification and characterization of a new gene of *Escherichia coli* K-12 involved in outer membrane permeability. Genetics 122, 491–501.
24. Aono, R., Negishi, T., and Nakajima, H. (1994). Cloning of organic solvent tolerance gene ostA that determines n-hexane tolerance level in *Escherichia coli*. Appl Environ Microbiol 60, 4624–4626.
25. Qin, C., Bu, X., Wu, X., and Guo, Z. (2003). A chemical approach to generate molecular diversity based on the scaffold of cyclic decapeptide antibiotic tyrocidine A. J Comb Chem 5, 353–355.
26. Backes, B. J., and Ellman, J. A. (1999). An alkanesulfonamide "safety-catch" linker for solid-phase synthesis. J. Org. Chem. 64, 2322–2330.
27. Yang, L., and Morriello, G. (1999). Solid phase synthesis of 'head-to-tail' cyclic peptides using a sulfonamide 'safety-catch' linker: the cleavage by cyclization approach. Tetrahedron.Lett. 40.
28. Parfait, R., de Bethune, M. P., and Cocito, C. (1978). A spectrofluorimetric study of the interaction between virginiamycin S and bacterial ribosomes. Mol Gen Genet 166, 45–51.
29. Kaiser, E., Colescott, R. L., Bossinger, C. D., and Cook, P. I. (1970). Color test for detection of free terminal amino groups in the solid-phase synthesis of peptides. Anal Biochem 34, 595–598.
30. Shin, Y., Winans, K. A., Backes, B. J., Kent, S. B. H., Ellman, J. A., and Bertozzi., C. R. (1999). Fmoc-based synthesis of peptide-thioesters: application to the total chemical synthesis of a glycoprotein by native chemical ligation. J. Am. Chem. Soc. 121, 11684–11689.

TABLE 1

Amino Acid Sequences of Antimicrobial Peptides

| Antibiotic | AA1[a] | AA2 | AA3 | AA4 | AA5 | AA6 | AA7 | AA8 | AA9 | AA10 |
|---|---|---|---|---|---|---|---|---|---|---|
| Pristinamycin IA | 3-Hpa | Thr | DAbu | Pro | N-Me-DMAPhe | 4-Oxo Pip | Phg | | | |
| Virginiamycin S1 | 3-Hpa | Thr | dAbu | Pro | N-MePhe | 4-Oxo Pip | Phg | | | |
| Patricin A | 3-Hpa | Thr | dAbu | Pro | N-MePhe | Pro | Phg | | | |
| Etamycin | 3-Hpa | Thr | dLeu | dHyp | Sar | DMLeu | Ala | PheSar | | |
| Compound 1 | Bz-3-Hpa | Thr | dAbu | Leu | dPhe | Pro | Phg | | | |
| Compound 2 | Bz-3-Hpa | Thr | Orn | Leu | dPhe | Pro | Phg | | | |
| Compound 3 | Pic | Thr | dAbu | Leu | dPhe | Pro | Phg | | | |
| Compound 4 | Pic | Thr | Orn | Leu | dPhe | Pro | Phg | | | |
| Compound 5 | 3-Hpa | Dap | Thr | Orn | Leu | dPhe | Pro | Phe | | |
| Compound 6 | 3-Hpa | Dap | dAbu | Orn | Leu | dPhe | Pro | Phg | | |
| Compound 7 | 3-Hpa | Dap | Orn | Leu | dPhe | Pro | Phg | | | |
| Compound 8 | 3-Hpa | Dap | dAbu | Pro | Phe | Pro | Phg | | | |
| Tyrocidine[b] | Gln | Tyr | Val | Orn | Leu | dPhe | Pro | Phe | dPhe | Asn |

[a]Abbreviations:
Abu, α-aminobutyric acid;
Dap, diaminopropionic acid;
DMLeu, N,β-dimethylleucine;
3-Hpa, 3-hydroxypicolonic acid;
Hyp, hydroxyproline;
N-MePhe, N-methylphenylalanine;
N-Me-DMAPhe, N-methyl-p-dimethylaminophenylalanine;
4-Oxo Pip, 4-Oxopipecolic acid;
Phg, phenylglycine;
Pic, picolinic acid;
Pip, pipecolic acid;
Sar, sarcosine;
PheSar, phenylsarcosine.
[b]Tyrocidine is a 10 amino acid macrocycle shown for comparison to the synthesized peptides.

TABLE 2

Inhibition of Bacterial Growth by Chimeric Antibiotics

| | Zone of Inhibition (cm) | | | | |
|---|---|---|---|---|---|
| Bacterial Strain | Quinupristin | Compound 5 | Compound 6[e] | Compound 7[e] | Compound 8 |
| *Escherichia coli* BAS901 | 2.2 | 1.1 | | | |
| *E. coli* BAS901/pUC19 | 2.2 | 1.1 | 1.2 | 1.2 | n.i. |
| *E. coli* BAS901/pUCVgb | n.i.[a] | 1.1 | 1.3 | 1.3 | n.i. |
| *Bacillus subtilis* 1A752 | 1.8 | 1.1 | | | |
| *B. subtilis* W23 | 2.1 | 0.9 | | | |
| *B. subtilis* L5706 | 2.1 | 0.8 | | | |
| *B. subtilis* 168 | 2.2 | 0.8 | | | |
| *Micrococcus luteus* | 2.7 | 1.0 | | | |
| *Enterococcus faecium* CP54-32 | 1.8 | 0.8 | | | |
| *Enterococcus faecalis* (ATCC 29212) | 1.8 | 0.75 | | | |
| *Enterococcus faecalis* (ATCC 51299)[b] | n.i. | n.i. | | | |
| *S. saprophyticus* (ATCC 15305) | 2.3 | 0.8 | | | |

TABLE 2-continued

Inhibition of Bacterial Growth by Chimeric Antibiotics

| Bacterial Strain | Zone of Inhibition (cm) | | | | |
|---|---|---|---|---|---|
| | Quinu-pristin | Compound 5 | Compound 6[e] | Compound 7[e] | Compound 8 |
| Staphylococcus epidermidis (ATCC 12228) | 3.4 | 0.85 | | | |
| Staphylococcus epidermidis (ATCC 14990) | 3.0 | 0.75 | | | |
| Staphylococcus aureus (ATCC 43300)[c] | n.i. | n.i. | | | |
| Staphylococcus aureus (ATCC 29213) | 2.3 | n.i. | | | |
| Staphylococcus aureus (ATCC 25923) | 2.2 | n.i. | | | |
| Staphylococcus aureus (ATCC 49476) | 2.6 | n.i. | | | |
| Streptococcus pneumoniae (ATCC 6305) | 2.1 | 0.8 | | | |
| Streptococcus pneumoniae (ATCC 49619) | 2.0 | n.i. | | | |
| E. coli (ATCC 25922) | n.i. | n.i. | | | |
| Salmonella enterica (ATCC 14028)[d] | n.i. | n.i. | | | |
| Haemophilus influenza | n.i. | n.i. | | | |

[a]n.i., no inhibition of growth.
[b]Vancomycin, aminoglycoside resistant *Enterococcus faecalis*.
[c]Methicillin resistant, oxacillin resistant *Staphylococcus aureus*.
[d]serovar Typhimurium.
[e]6 and 7 were analyzed following cyclization without further purification.

TABLE 3

MIC Values for Quinupristin and 5 against Susceptible Bacteria

| Organism | MIC (µg/ml) | |
|---|---|---|
| | Quinupristin | Compound 5 |
| E. coli BAS901/pUC19 | 4 | 32 |
| E. coli BAS901/pUC19ermB | 16 | 32 |
| E. coli BAS901/pUCVgb | >256 | 32 |
| Staphylococcus aureus RN4220/pJIM2246 | 2 | 256 |
| Staphylococcus aureus RN4220/pJIM2246ΩermB | 8[a] | 256 |
| Staphylococcus aureus RN4220/pJIM2246Ωvgb | 8 | 256 |
| Staphylococcus aureus (ATCC 29213) | 4 | 256 |
| Staphylococcus epidermidis (ATCC 12228) | 0.5 | 64 |
| Staphylococcus epidermidis (ATCC 14990) | 1 | 64 |
| Staphylococcus saprophyticus (ATCC 15305) | 8 | 64 |
| Enterococcus faecalis (ATCC 29212) | 8 | 128 |
| Streptococcus pneumoniae (ATCC 6305) | 1 | 32 |
| Streptococcus pneumoniae (ATCC 49619) | 0.5 | 128 |

[a]Indicates induction with quinupristin (1 µg/ml).

We claim:

1. A cyclic peptide antibiotic wherein the antibiotic is a streptogramin Type B derivative and comprises the replacement of an enzyme sensitive ester bond with a stable bond selected from the group consisting of an amide, N-methyl amide, enamine and sulfonamide bond.

2. An antibiotic according to claim 1 wherein the antibiotic is resistant to cleavage by Vgb enzyme.

3. A cyclic peptide according to claim 1 having a structure selected from the structures of compounds 5, 6, 7 and 8 have the structures:

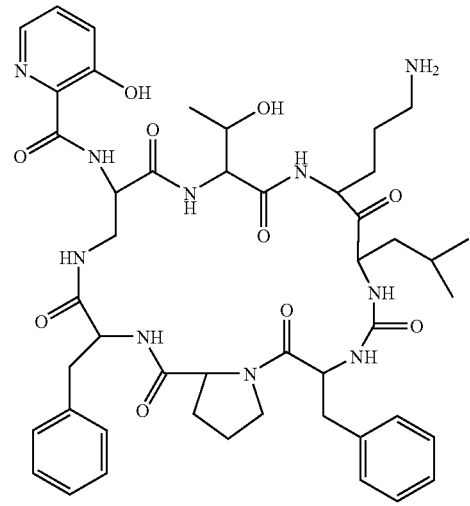

5

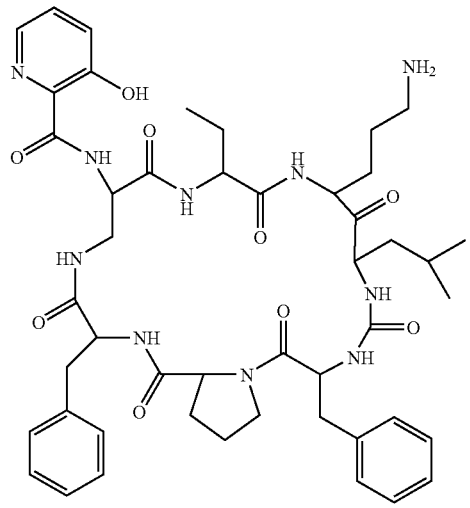

6

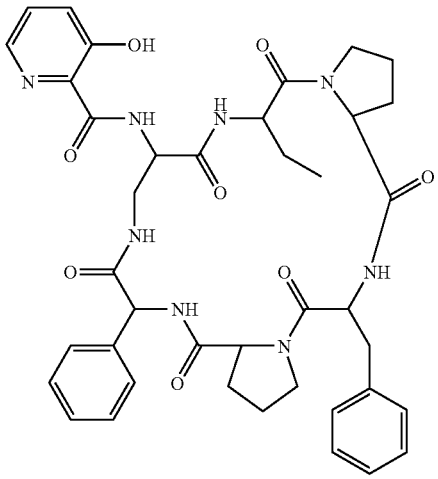

7

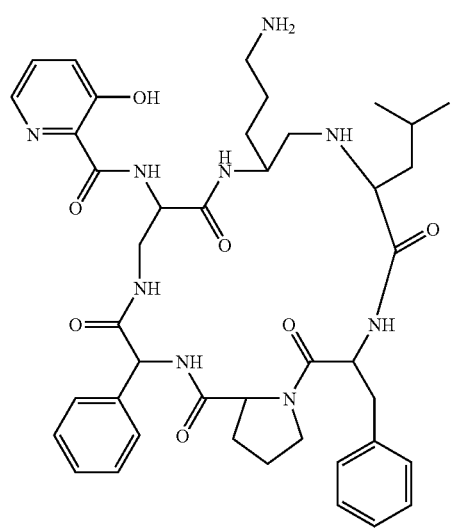

8

4. A cyclic peptide antibiotic according to claim 3 having the structure of compound 5.

5. A cyclic peptide antibiotic according to claim 3 having the structure of compound 6.

6. A cyclic peptide antibiotic according to claim 3 having the structure of compound 7.

7. A cyclic peptide antibiotic according to claim 3 having the structure of compound 8.

8. An antibiotic composition comprising a cyclic peptide antibiotic as defined in claim 1 and a pharmaceutically acceptable carrier.

9. An antibiotic composition according to claim 8, further comprising a second antibiotic.

10. An antibiotic composition according to claim 9 having a format selected from the group consisting of a pill, tablet, capsule, liquid, powder, vapor and suppository.

11. An animal feed composition comprising at least one antibiotic as defined in claim 1.

* * * * *